United States Patent [19]

Koyama

[11] Patent Number: 4,784,848

[45] Date of Patent: Nov. 15, 1988

[54] WAVING LOTION COMPOSITION

[75] Inventor: Takahiro Koyama, Hoya, Japan

[73] Assignee: Daicel Chemical Industries, Ltd., Osaka, Japan

[21] Appl. No.: 118,200

[22] Filed: Nov. 6, 1987

Related U.S. Application Data

[63] Continuation-in-part of Ser. No. 866,186, May 22, 1986, abandoned.

[30] Foreign Application Priority Data

Jun. 14, 1985 [JP] Japan ................................ 60-128370

[51] Int. Cl.⁴ ................................................ A61K 7/09

[52] U.S. Cl. ........................................ 424/71; 424/72

[58] Field of Search .................................... 424/71, 72

[56] References Cited

U.S. PATENT DOCUMENTS

| | | | |
|---|---|---|---|
| 3,935,868 | 2/1976 | Zeffreu et al. | 424/71 |
| 3,966,928 | 6/1976 | Douglass | 424/71 |
| 4,041,033 | 8/1977 | Douglass | 424/71 |
| 4,137,302 | 1/1979 | Humbert | 424/71 |
| 4,153,681 | 5/1979 | Shiba | 424/72 |
| 4,210,161 | 7/1980 | Wagman | 424/71 |
| 4,218,435 | 8/1980 | Shiba | 424/72 |
| 4,426,518 | 1/1984 | Omiya | 536/98 |
| 4,445,521 | 5/1984 | Grollier et al. | 424/71 |

FOREIGN PATENT DOCUMENTS 960155 6/1964 United Kingdom .

OTHER PUBLICATIONS

Davidson, *Handbook of Water-Soluble Gums and Resins*, pp. 4–2 thru 4–3 (1980).

*Cosmetic Materials*, pp. 120–129 (1963).

*Primary Examiner*—Jerome D. Goldberg

*Assistant Examiner*—F. Krosnick

*Attorney, Agent, or Firm*—Flynn, Thiel, Boutell & Tanis

[57] ABSTRACT

A waving lotion composition is thickened and is more spreadable when there is used, as a thickening and spreading agent, an alkali metal salt or ammonium salt of carboxymethylcellulose (CMC) having an etherificiation degree of 2.4 or more.

3 Claims, No Drawings

WAVING LOTION COMPOSITION

CROSS-REFERENCE TO RELATED APPLICATION

This is a continuation-in-part of Ser. No. 866,186, filed May 22, 1986, now abandoned.

FIELD OF THE INVENTION

The present invention relates to waving lotions, and more particularly to a thickening spreader which is an important ingredient of waving lotions.

DESCRIPTION OF PRIOR ART

Although the principle of permanent waving of hair is not fully understood, it is believed that cystine bonds (-S-S-) in the hair play an important role. Usually, first and second liquids are used to obtain a permanent wave effect. The first liquid contains an alkaline solution of a thioglycolate as a reducing agent. Hydrogen bonds, salt bonds and cystine bonds in the hair are broken by moisture, the alkali and the reducing agent of the first liquid, whereby the hair is softened. Usually, the second liquid contains a sodium bromate solution as an oxidizing agent. After the hair is treated with the first liquid, the latter is washed away by using an acidic rinse and the hair is then treated with the second liquid, whereby the salt bonds are reformed by the neutralization of the alkali and the cystine bonds are reformed by the action of the oxidizing agent. Further, new hydrogen bonds are formed as the hair is dried, whereby the hair is waved.

Although the reducing power is of prime importance among the various functions and qualities required of the first liquid (waving lotion), there are numerous subordinate requisites, among which, a thickening spreader ingredient has an important effect. The principal object of the thickening spreader is to impart moderate viscosity and spreadability to the first liquid. Examples of the thickening spreaders which have been conventionally used include cellulose derivatives, polysodium acrylate, polyisobutylene, polyethylene glycol, polyvinyl alcohol and natural paste.

Various functions, such as, long-term viscosity stability at a pH of as high as 9 to 10, moderate flow characteristics and spreadability, easy washability with acidic rinses, dissolution workability during the preparation of the waving lotion and high transparency, are required of the thickening spreaders for waving lotions.

Conventional thickening spreaders have not met all of these requirements.

We have made studies to find a thickening spreader which can meet all of these requirements and have discovered the present invention.

SUMMARY OF THE INVENTION

The present invention relates to a waving lotion characterized by containing an alkali metal salt or an ammonium salt of carboxymethylcellulose (hereinafter referred to as CMC) having a degree of etherification (hereinafter referred to as DS) of at least 2.4, as a thickening spreader.

DETAILED DESCRIPTION

In a waving lotion composition, the invention provides an improvement comprising the incorporation of an alkali metal salt or ammonium salt of carboxymethylcellulose (CMC) having an etherification degree of 2.4 to 3.0, as an ingredient effective for improving the thickening and spreading properties of the waving lotion composition.

It is preferable that CMC is contained in the composition in an amount of 0.1 to 3.0 percent by weight, more advantageously 0.1 to 2.0 percent by weight, most advantageously 0.3 to 1.5 percent by weight, based on the weight of the composition.

In the waving lotion composition of the invention, conventional components are used in addition to the above defined CMC. CMC serves as a thickening spreader in the waving lotion composition.

Examples of the CMC having a DS of from 2.4 to 3.0 which can be used in the present invention include those prepared from an alkaline cellulose and monochloroacetic acid by a multi-stage addition method or a multi-stage reaction method disclosed in, for example, Japanese Patent Laid-Open Nos. 45201/1983 and 176202/1983. Alkali metal salts or ammonium salts of CMC having a DS of 2.0 or below which have been conventionally used have a poor resistance to alkalis and, hence, the first liquid having a high pH, due to the addition of an alkali, undergoes a lowering in its viscosity. Since the maximum DS is theoretically 3.0, CMC having a DS of 2.4 to 3.0 can be used in the present invention. However, the closer is the DS to the theoretical value of 3.0, the more difficult is its production on an industrial scale and the higher is its cost. Accordingly, the preferred DS value is in the range of 2.4 to 2.95.

Preferably, a 1% by weight aqueous solution of the alkali metal salt or ammonium salt of CMC employed in the present invention has a viscosity of 10 to 10,000 cps at 20° C.

Examples of the alkali metal salts of CMC include lithium, potassium and dosium salts. Among them, the sodium salt, which is widely prepared on an industrial scale, is usually used. The ammonium salt of CMC of the present invention also has an excellent function similar to that of the sodium salt.

The waving lotion composition, according to the invention, contains from 45 to 90 percent by weight of purified water and the balance is conventional ingredients used in hair waving lotion compositions.

The conventional ingredients include (a) a reducing agent for treating hair, for example, ammonium thioglycolate, (b) a conventional amount of an alkali, (c) 0.1 to 5.0 percent by weight of a surfactant and, optionally, (d) other additives, such as, a cheating agent, an antioxidant, a wetting agent, an amino acid, a perfume and/or coloring matter. The reducing agent comprises (a-1) 5 to 30 percent by weight of ammonium, potassium or sodium thioglycolate or (a-2) 10 to 40 percent by weight of cystein, both percentages being based on the weight of the hair waving lotion composition. The alkali includes aqueous ammonia, ethanolamine, ammonium carbonate, sodium hydroxide and potassium hydroxide and it serves to adjust the pH value of the composition to the range of 8.5 to 10.5. The surfactant is chosen so that the resulting composition will not be an irritant to the human body, that the composition can be emulsified and that the active ingredients will impregnate the hair.

The following examples will further illustrate the present invention. The effects of the present invention are also described below.

EXAMPLES 1 TO 2 AND COMPARATIVE EXAMPLES 1 TO 5

Each of waving lotions having the following compositions and containing the sodium salt of CMC having a DS of 2.4 and 2.8, respectively, as a thickening spreader, were prepared. For the purpose of comparison, waving lotions having the following compositions and containing sodium salts of CMC having a DS of 0.9 and 1.5, respectively, hydroxyethylcellulose, tragacanth gum and polysodium acrylate, as a thickening spreader, also were prepared. The thickening spreaders were evaluated with respect to their workability during dissolution, transparency, long-term viscosity stability and washability with acidic rinse. The types of the thickening spreaders tested are listed in Table 1, and the evaluation results are shown in Table 2.

| Composition of waving lotion | |
|---|---|
| ammonium thioglycolate (50% aqueous solution) | 10.0 wt. % |
| ammonia liquor (28% aqueous solution of ammonia) | 1.5 |
| propylene glycol | 5.0 |
| thickening spreader | 0.5 |
| purified water | 83.0 |
| cheating agent | an appropriate quantity |

TABLE 1

| | Type of thickening spreader |
|---|---|
| Example 1 | sodium salt of CMC having a DS of 2.4 |
| Example 2 | sodium salt of CMC having a DS of 2.8 |
| Comp. Ex. 1 | sodium salt of CMC having a DS of 0.9 |
| Comp. Ex. 2 | sodium salt of CMC having a DS of 1.5 |
| Comp. Ex. 3 | hydroxyethylcellulose |
| Comp. Ex. 4 | tragacanth gum |
| Comp. Ex. 5 | polysodium acrylate |

TABLE 2

| | Evaluated function | | | |
|---|---|---|---|---|
| No. | Workability during dissolution 1 | Trans-parency | Long-term viscosity stability 2 | Washability with acidic rinse |
| Ex. 1 | o | o | o | o |
| Ex. 2 | o | o | o | o |
| Comp. Ex. 1 | x | x | x | Δ |
| Comp. Ex. 2 | Δ | Δ | x | Δ |
| Comp. Ex. 3 | x | Δ | o | x |
| Comp. Ex. 4 | Δ | x | o | Δ |
| Comp. Ex. 5 | x | o | o | Δ |

Evaluation Ratings:
o . . . good
Δ . . . intermediate between good and bad
x . . . bad Note 1: Workability during dissolution The thickening spreader is evaluated as being "good", when it can be relatively quickly dissolved without requiring heating and it scarcely forms undissolved lumps.

Note 2: Long-term viscosity stability The spreader is evaluated as being "good", when it scarcely causes changes in viscosity after being left to stand for 6 months at room temperature.

EXAMPLES 3 and 4 and Comparative Examples 6 to 8

Five waving lotion compositions were prepared using the below listed ingredients. The compositions were examined in the same way as described in Example 1. The compositions were different from one another only as regards the etherification degree of "sodium carboxymethylcellulose". The various sodium carboxymethylcellulose samples that were tested are listed in Table 3. The test results are shown in Table 4.

| Ingredients of the waving lotion composition | percent by weight |
|---|---|
| 50 wt. % aqueous solution of ammonium thioglycolate | 24.0 |
| ammonium carbonate | 5.0 |
| ammonium hydrogencarbonate | 2.0 |
| perfume oil | 0.5 |
| 1,4-nonylphenol having 10 oxyethylene units (nonionic surfactant) | 0.6 |
| sodium carboxymethylcellulose | 1.0 |
| purified water | 66.9 |

TABLE 3

| test No. | etherification degree of sodium carboxymethyl cellulose |
|---|---|
| Example 3 | 2.4 |
| Example 4 | 2.6 |
| Comparative Example 6 | 2.2 |
| Comparative Example 7 | 2.0 |
| Comparative Example 8 | 1.8 |

TABLE 4

| | Invention Examples | | Comparative Examples | | |
|---|---|---|---|---|---|
| Evaluation | 3 | 4 | 6 | 7 | 8 |
| workability during dissolution | o | o | Δ | Δ | Δ |
| transparency | o | o | o | Δ | Δ |
| long term viscosity stability | o | o | x | x | x |
| washability with acidic rinse | o | o | Δ | Δ | Δ |

The embodiments of the invention in which an exclusive property or privilege is claimed are defined as follows:

1. In a lotion composition useful in a process for the permanent waving of hair, said composition comprising an alkaline aqueous solution of a reducing agent for treating hair and a thickening spreader, the improvement which comprises: said thickening spreader is a salt of a carboxymethylcellulose selected from the group consisting of the sodium, potassium, lithium and ammonium salts of carboxymethylcellulose, said salt of carboxymethylcellulose having an etherification degree of from 2.4 to 3.0, a one percent by weight aqueous solution of said salt of carboxymethylcellulose having a viscosity, at 20° C., of from 10 to 10,000 cps, said lotion composition containing from 0.1 to 3.0 percent by weight of said salt of carboxymethylcellulose.

2. A composition as claimed in claim 1, which contains 0.3 to 1.5 percent by weight of said salt of carboxymethylcellulose.

3. A composition as claimed in claim 1, in which said salt of carboxymethylcellulose has an etherification degree of 2.4 to 2.95.

* * * * *